(12) United States Patent
Blum (10) Patent No.: US 10,148,767 B2
(45) Date of Patent: Dec. 4, 2018

(54) METHOD AND MOBILE UNIT UPDATING THE CONFIGURATION OF A MEDICAL TECHNOLOGY APPARATUS WITHOUT AN INTERNET CONNECTION

(71) Applicant: Siemens Healthcare GmbH, Erlangen (DE)

(72) Inventor: Thomas Blum, Nuenkirchen A. Br. (DE)

(73) Assignee: Siemens Healthcare GmbH, Erlangen (DE)

( * ) Notice: Subject to any disclaimer, the term of this patent is extended or adjusted under 35 U.S.C. 154(b) by 39 days.

(21) Appl. No.: 15/422,655

(22) Filed: Feb. 2, 2017

(65) Prior Publication Data
US 2017/0220756 A1 Aug. 3, 2017

(30) Foreign Application Priority Data
Feb. 3, 2016 (DE) .................. 10 2016 201 634

(51) Int. Cl.
*G06F 9/445* (2018.01)
*H04L 29/08* (2006.01)
*G06F 8/65* (2018.01)
*G16H 40/40* (2018.01)

(52) U.S. Cl.
CPC .............. *H04L 67/141* (2013.01); *G06F 8/65* (2013.01); *G16H 40/40* (2018.01); *H04L 67/04* (2013.01); *H04L 67/1074* (2013.01); *H04L 67/1095* (2013.01); *H04L 67/12* (2013.01); *H04L 67/34* (2013.01)

(58) Field of Classification Search
None
See application file for complete search history.

(56) References Cited

U.S. PATENT DOCUMENTS

| | | | |
|---|---|---|---|
| 2009/0058635 A1* | 3/2009 | LaLonde | A61N 1/37282 340/539.11 |
| 2010/0299719 A1* | 11/2010 | Burks | G06F 9/44505 726/3 |
| 2013/0036415 A1* | 2/2013 | Birtwhistle | G06F 8/65 717/173 |
| 2013/0211547 A1* | 8/2013 | Buchdunger | G05B 19/0426 700/11 |
| 2014/0282470 A1 | 9/2014 | Buga et al. | |

* cited by examiner

*Primary Examiner* — Daxin Wu
(74) *Attorney, Agent, or Firm* — Schiff Hardin LLP (57) ABSTRACT

A mobile unit with a memory is temporarily connected to a medical technology apparatus is temporarily connected to a central storage device for data transmission. When the mobile unit is connected to the medical technology apparatus, a real configuration of the medical technology apparatus is compared with a local virtual image of the configuration of the medical technology apparatus held in the memory of the mobile unit. Depending on this comparison, the local configuration and/or the real configuration are updated. When the mobile unit is connected to the central storage device, the local configuration is compared with a central virtual image of the configuration of the medical technology apparatus. Depending on this comparison, the central configuration and/or the local configuration are updated. Via the indirect route of the local configuration this enables the real configuration and the central configuration to be mutually updated.

12 Claims, 3 Drawing Sheets

FIG 1

METHOD AND MOBILE UNIT UPDATING THE CONFIGURATION OF A MEDICAL TECHNOLOGY APPARATUS WITHOUT AN INTERNET CONNECTION

BACKGROUND OF THE INVENTION

Field of the Invention

The present invention concerns a method for updating a real configuration of a medical technology apparatus and/or a central virtual image of the configuration of the medical technology apparatus stored in a central storage device.

The present invention is further based on a mobile unit with a memory for implementing such a method.

Description of the Prior Art

Medical technology apparatuses—for example x-ray apparatuses, ultrasound systems, magnetic resonance apparatuses and others—are more and more controlled by software. By contrast with many electronic devices for consumers, the software in medical technology apparatuses is not merely installed once on the system, but must continue to be maintained and updated during the lifetime of the respective medical technology apparatus. The underlying reasons for this are diverse, and extend from simple, small error corrections to serious safety-critical situations or regular security updates to avoid the risk of virus infections and data theft.

Furthermore, with medical technology apparatuses, for many maintenance tasks it is necessary to be able to gain access to a medical technology apparatus that is operated on the operator's premises. Examples of these types of accesses are usage data, logging and tracing information and image data from patients. Usage data can be used to improve the product or to predict a failure of replacement parts. Logging and tracing information can be used within the framework of fault tracing. Image data from patients can be used for checking imaging quality, for example.

It is possible to update the real configuration of the medical technology apparatus and/or of the central virtual image of the configuration of the medical technology apparatus stored in a central storage device relatively easily when the medical technology apparatus is regularly connected to the Internet or even permanently connected to the Internet. If, however, the medical technology apparatus is embodied as a mobile or also non-stationary apparatus that is not connected to the Internet, the updating of the real configuration of the medical technology apparatus and/or of the central virtual image of the configuration of the medical technology apparatus held in a central storage device is only possible with significant effort. This situation can arise in developing countries, but can also occur in other scenarios.

In order to still be able to carry out this type of updating for medical technology apparatuses that are not connected to the Internet, updates are performed via storage media (for example USB memory sticks or CDs or DVDs) for example, which are temporarily connected to the medical technology apparatus by a service technician. This activity is time-consuming and prone to errors.

The same applies to maintenance tasks for medical technology apparatuses that are not connected to the Internet. Here as well, access to the medical technology apparatus and data capture turn out to be extremely laborious. In many cases data capture is not even possible with sensible outlay. If it is undertaken despite this, this activity is also time-consuming and prone to errors.

SUMMARY OF THE INVENTION

An object of the present invention is to create options by which the updating of the real configuration of the medical technology apparatus and/or of the central virtual image of the configuration of the medical technology apparatus held in a central storage device is possible in a simple and reliable manner, without the medical technology apparatus having to be connected to the Internet.

In accordance with the invention a method for updating a real configuration of a medical technology apparatus and/or a central virtual image of the configuration of the medical technology apparatus held in a central storage device is implemented by a) a mobile unit including a memory being connected by a data connection for a time to the medical technology apparatus and for a time to the central storage device;

b) then, when the mobile unit is connected to the medical technology apparatus, by the real configuration of the medical technology apparatus being compared with a local virtual image of the configuration of the medical technology apparatus held in a memory of the mobile unit and, depending on this comparison, the local virtual image of the configuration of the medical technology apparatus and/or of the real configuration of the medical technology apparatus being updated; and c) then, when the mobile unit is connected to the central storage device, by the local virtual image of the configuration of the medical technology apparatus being compared with the central virtual image of the configuration of the medical technology apparatus and, depending on this comparison, the central virtual image of the configuration of the medical technology apparatus and/or of the local virtual image of the configuration of the medical technology apparatus being updated.

This method according to the invention allows updating of the real configuration of the medical technology apparatus and the updating of the virtual image of the configuration of the medical technology apparatus held in the central storage device are decoupled from one another in time. The storage of the local virtual image of the configuration of the medical technology apparatus in the mobile unit allows the physical transportation of the mobile unit from the site of the medical technology apparatus to another site at which there is access to the Internet, or generally to a computer network, while at the same time transporting the virtual image of the configuration of the medical technology apparatus. This, in turn, allows the local virtual image to be present for a time at the site of the medical technology apparatus and for a time at the site with access to the Internet.

The updating of step b) can be designed as required. Preferably the updating of step b) occurs such that, after the updating, the local virtual image of the configuration of the medical technology apparatus and the real configuration of the medical technology apparatus match.

In a similar way the updating of step c) can also be designed as required. Preferably the updating of step c) occurs such that, after the updating, the central virtual image of the configuration of the medical technology apparatus and the local virtual image of the configuration of the medical technology apparatus match.

Preferably the mobile unit is connected to the medical technology apparatus via a peer-to-peer connection for transmission of data. The peer-to-peer connection can be realized for example as a cable connection, for example via a network cable or a USB interface. As an alternative a wireless connection, for example via a Bluetooth connection or an NFC connection is possible. NFC, as technical experts know, stands for Near Field Communication.

Preferably the mobile unit is also connected to the central storage device for transmission of data via a link to a computer network. The link can be made directly or indirectly via a connecting device. For example the mobile unit can be connected directly to the computer network or to a PC or to a similar calculation unit, which in its turn is connected to the computer network. The computer network can be the Internet for example.

In the simplest case the mobile unit is embodied purely as a storage unit. Preferably however the mobile unit includes a logic unit. This is because it is then possible for the logic unit, when the mobile unit is connected to the medical technology apparatus, to behave like the central storage device in relation to communication with the medical technology apparatus, and for the logic unit, when the mobile unit is connected to the central storage device, to behave like the medical technology apparatus in relation to communication with the central storage device.

In other words: When the logic unit is connected to the medical technology apparatus, the medical technology apparatus does not "notice" at all that it is not connected to the central storage device, but to the mobile unit. The communication between the mobile unit and the medical technology apparatus thus occurs from the standpoint of the medical technology apparatus as if the medical technology apparatus were connected to the central storage device. In a similar way the central storage device, in the event of the mobile unit being connected to the central storage device, does not "notice" at all that it is not connected to the medical technology apparatus, but to the mobile unit. The communication between the mobile unit and the central storage device thus occurs from the standpoint of the central storage device as if the medical technology apparatus were connected to the central storage device.

In a preferred embodiment, the data connection between the mobile unit and the medical technology apparatus is made wirelessly. This is possible because the mobile unit can establish the connection to the medical technology apparatus autonomously as soon as the mobile unit, in relation to the wireless data connection to the medical technology apparatus, is brought within range of the medical technology apparatus.

In a similar way it is preferred that the data connection between the mobile unit and the central storage device be made wirelessly. This is because this makes it possible for the mobile unit to establish the connection to the central storage device autonomously as soon as the mobile unit, in relation to the wireless data connection to the central storage device, is brought within range of the central storage device.

In accordance with the invention a mobile unit with a memory is embodied by a local virtual image of a real configuration of a medical technology apparatus being held in the memory of the mobile unit.

The advantageous embodiments the mobile unit essentially correspond to the advantageous embodiments of the method.

The mobile unit preferably has a logic unit programmed such that, the logic unit, when the mobile unit is connected to the medical technology apparatus, then behaves like a central storage device in relation to communication with the medical technology apparatus, and the logic unit, when the mobile unit is connected to the central storage device, then behaves like the medical technology apparatus in relation to communication with the central storage device.

To establish the data connection to the medical technology apparatus, the logic unit further includes an interface set up wirelessly. This then enables the mobile unit to be designed such that the logic unit can be programmed to allow the mobile unit to establish the connection to the medical technology apparatus autonomously as soon as the mobile unit, in relation to the wireless interface to the medical technology apparatus, is brought within range of the medical technology apparatus.

In a similar way the logic unit, to establish the data connection to the central storage device, preferably includes an interface set up wirelessly. This then enables the mobile unit to be programmed so that the mobile unit establishes the connection to the central storage device autonomously as soon as the mobile unit, in relation to the wireless interface to the central storage device set up wirelessly, is brought within range of the central storage device.

The mobile unit can be embodied in various formats, such as a smartphone, a tablet PC, a notebook, a laptop, or a PC.

DESCRIPTION OF THE PREFERRED EMBODIMENTS

Figure 1:
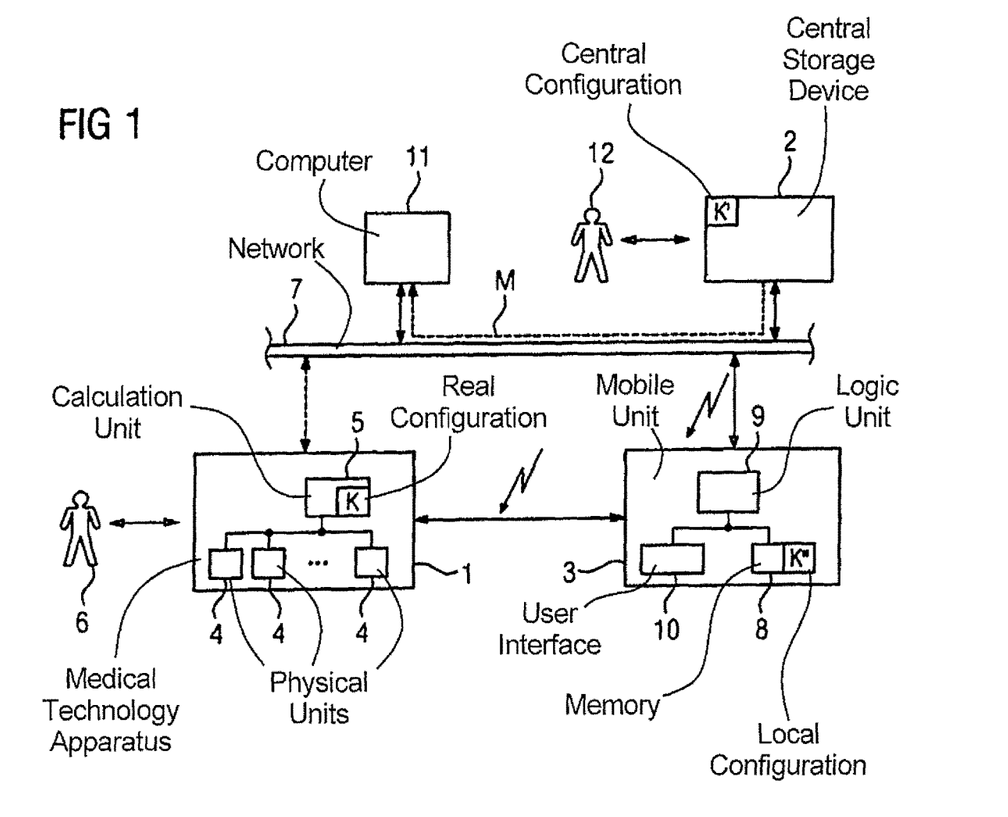
FIG. 1 shows an overview of a system composed of a medical technology apparatus, a central storage device and a mobile unit.

In accordance with FIG. 1 an inventive system has three basic components. The components of the system are a (real) medical technology apparatus 1, a central storage device 2 and a mobile unit 3. In principle each of the components 1 to 3 can communicate with any other component 1 to 3. Thus in principle both communication between the medical technology apparatus 1 and the central storage device 2 and also communication between the medical technology apparatus 1 and the mobile unit 3 and also communication between the central storage device 2 and the mobile unit 3 is possible. All these communications will be explained in greater detail below.

The medical technology apparatus 1 can be embodied as an ultrasound device, as an x-ray apparatus, as a magnetic resonance apparatus or as another medical technology apparatus. Regardless of its actual embodiment, the medical technology apparatus 1 in accordance with FIG. 1 has a number of physical units 4. Many of the physical units 4 (even if not necessarily all of the physical units 4) are software-programmed.

A configuration K of the medical technology apparatus 1 is stored in a calculation unit 5 of the medical technology apparatus 1—which as such is likewise a physical unit of the medical technology apparatus 1.

The configuration K includes at least the following components:

An individual identification of the type of each of the physical units 4, which identifies the type of the respective physical unit;

An individual identification of the type of each installed software (including the respective software status, i.e. which update);

Settings of the medical technology apparatus 1 made by the user 6 of the medical technology apparatus 1 or by another person;

Software releases;

Logging data and tracing data.

Logging data are events that have occurred during operation of the medical technology apparatus 1, and in particular have been registered with the time of their occurrence. The events include in particular errors that have occurred. Tracing data are usage processes. They thus specify the times at which the medical technology apparatus 1 has been operated in a particular way.

The configuration K can further include the following components:

- An individual identification of the respective medical technology apparatus 1 as such, which is also only issued once in each case for medical technology apparatuses 1 of identical construction;
- An individual identification of the respective physical units 4, which is also only issued once in each case for physical units 4 (even in different apparatuses) of identical construction;
- An update run that reflects the sequence in which software updates have been carried out; and
- Usage data acquired or established by means of the medical technology apparatus 1, for example image data (where necessary in anonymized form).

Where necessary the configuration K can also include additional data. The totality of the data contained in the configuration K—i.e. the configuration K in its entirety—gives a very precise picture of the medical technology apparatus 1. This is known to persons skilled in the art.

The medical technology apparatus is configured within the framework of its installation and commissioning. The settings and releases are also carried out within the framework of the installation and commissioning. After the installation and commissioning the configuration K is complete. The configuration K held in the calculation unit 5 is the real configuration of the medical technology apparatus 1. It is referred to below for short as real configuration K. The access to real configuration K can be protected against unauthorized access, for example by a user name and a password, by checking for access only from a specific IP address etc. This is generally known to persons skilled in the art.

The central storage device 2 is a separate device from the medical technology apparatus 1. The central storage device 2 can for example involve a server provided by the manufacturer of the medical technology apparatus 1 or can involve Cloud storage. Regardless of its actual embodiment, the central storage device 2 is linked to a computer network 7, so that access to the central storage device 2 is possible via the computer network 7. The computer network 7 can in particular be the Internet.

A configuration K' of the medical technology apparatus 1 is likewise held in the central storage device 2. With the configuration K' however it is not always and under all circumstances guaranteed that the configuration K' matches the real configuration K. The configuration K' held in the central storage device 2 therefore only represents a virtual image of the configuration of the medical technology apparatus 1. The reason that it is referred to as a virtual image is that the image stored in the central storage device 2 is not related to the central storage device 2, but to the medical technology apparatus 1. The configuration K' held in the central storage device 2, in terms of its approach however, comprises data of equal value to the real configuration K, i.e. the type identifications of the physical units 4 of the medical technology apparatus 1, the type identifications of the software (including the respective software status) installed on the medical technology apparatus 1, settings of the medical technology apparatus 1, releases of software, logging data and tracing data and possibly also individual identifications of the medical technology apparatus 1 as such and/or of the physical units 4 of the medical technology apparatus 1 and an update run. Although the data—with the exception of the individual identification of the medical technology apparatus 1 as such—does not necessarily have to be a 1:1 match with the corresponding data of the real configuration K, it does however serve the same purpose. The configuration K' held in the central storage device 2 will be referred to below for short as the central configuration K'.

Usually the respective central configuration K' is held in the central storage device 2 in each case for many medical technology apparatuses 1. For each stored central configuration K', however, it is—of course—noted to which real medical technology apparatus 1 the respective central configuration K' is related. Subsequently, therefore, reference is only made to the one central configuration K', which is related to the medical technology apparatus 1 considered here.

Usually the central configuration K' is stored by the manufacturer of the medical technology apparatus 1 in the central storage device 2. For example the manufacturer can store the central configuration K' in the central storage device 2 independently of installation and commissioning. It is also possible, within the framework of installation and commissioning of the medical technology apparatus 1, for the medical technology apparatus 1 to be registered by the user 6 with the central storage device 2 and for the central configuration K' to be created within the framework of the registration, in particular by transmission of the real configuration K to the central storage device 2. Independently of the manner in which the central configuration K' is stored in the central storage device 2, a unique assignment of the central configuration K' to the respective medical technology apparatus 1 is made, to which the central configuration K' is related.

In a similar way to access to the real configuration K, access to the central configuration K' can be protected against unauthorized access. The protection mechanisms are similar to those for the real configuration K.

The mobile unit 3 is a device separate from both the medical technology apparatus 1 and also from the central storage device 2. In the simplest case the mobile unit 3 is embodied as a simple memory 8. In this case processes that will be explained later in connection with FIG. 3 will be actuated by the medical technology apparatus 1. Preferably however, as depicted in FIG. 1, in addition to the memory 8, the mobile unit 3 has a logic unit 9 and a user interface 10. For example the mobile unit 3 can be embodied as a smartphone, as a tablet PC, as a notebook, as a laptop or as a PC. In this case, in accordance with the explanation given below for FIG. 3, the mobile unit 3 itself can assume an active role.

There is likewise a configuration K" of the medical technology apparatus 1 held in the mobile unit 3 (especially in its memory 8). With the configuration K" however—just as with the central configuration K'—it is not guaranteed always and under all circumstances that the configuration K" matches the real configuration K. The configuration K" held in the mobile unit 3 therefore likewise only represents a virtual image of the configuration of the medical technology apparatus 1. The reason for the designation as virtual image—as with the central configuration K'—is also that the image stored in the mobile unit 3 is not related to the mobile unit 3, but to the medical technology apparatus 1. The configuration K" held in the mobile unit 3 however, in terms of its approach, comprises equivalent data to the real configuration K, i.e. the type identifications of the physical units 4 of the medical technology apparatus 1, the type identifications of the software stored on the medical technology apparatus 1 (including the respective software version), settings of the medical technology apparatus 1, releases of software, logging data and tracing data and possibly also individual identifications of the medical technology apparatus 1 as such and/or of the physical units 4 of the medical technology apparatus 1 and an update run. Although the data—with the exception of the individual identification of the medical technology apparatus 1 as such—does not necessarily have to correspond 1:1 with the corresponding data of the real configuration K, it does however serve the same purpose.

The configuration K" held in the mobile unit 3 will be referred to below for short as the local configuration K". Furthermore, because of the fact that mobile unit 3 is not only a different unit from the real medical technology apparatus 1, but is also a different unit from the central storage device 2, it is not guaranteed always and under all circumstances that the configuration K" matches the central configuration K'. For this reason a distinction is made between the local configuration K" and the central configuration K'.

It is possible for the local configuration K" for a single medical technology apparatus 1 to be exclusively stored in the mobile unit 3. As an alternative it is possible that the local configurations K" for a number of medical technology apparatuses 1 are held in the mobile unit 3. If the local configurations K" for a number of medical technology apparatuses 1 are held in the mobile unit 3, these will however be managed separately from one another by the mobile unit 3. Furthermore in this case the real medical technology apparatus 1 to which the respective local configuration K" relates is noted in the mobile unit 3 for each stored local configuration K". Subsequently reference is only made to the one local configuration K", which is related to the medical technology apparatus 1 currently being considered.

The local configuration K" can be held in a different manner in the mobile unit 3. For example the mobile unit 3 can have a data connection to the computer network 7. In this case the local configuration K" can be stored in the mobile unit 3 by transmitting the central configuration K' to the mobile unit 3. As an alternative the mobile unit 3 can have a data connection to the medical technology apparatus 1. In this case the local configuration K" can be stored in the mobile unit 3 by transmitting the real configuration K to the mobile unit 3. Regardless of the manner in which the local configuration K" is stored in the mobile unit 3, a unique assignment of the local configuration K" to the respective medical technology apparatus 1, to which the local configuration K" is related, is made.

In a similar way to the real configuration K and to the central configuration K', the local configuration K" can be protected against unauthorized access. The protection mechanisms are similar to those for the real configuration K and the central configuration K'.

Direct communication between the real medical technology apparatus 1 and the central storage device 2 is initially explained below in connection with FIG. 2, i.e. the communication that would occur if the real medical technology apparatus 1 were connected directly via the computer network 7 to the central storage device 2. This communication is not the subject matter of the present invention as such. However understanding said communication makes it easier to understand the present invention.

Figures 2, 3:
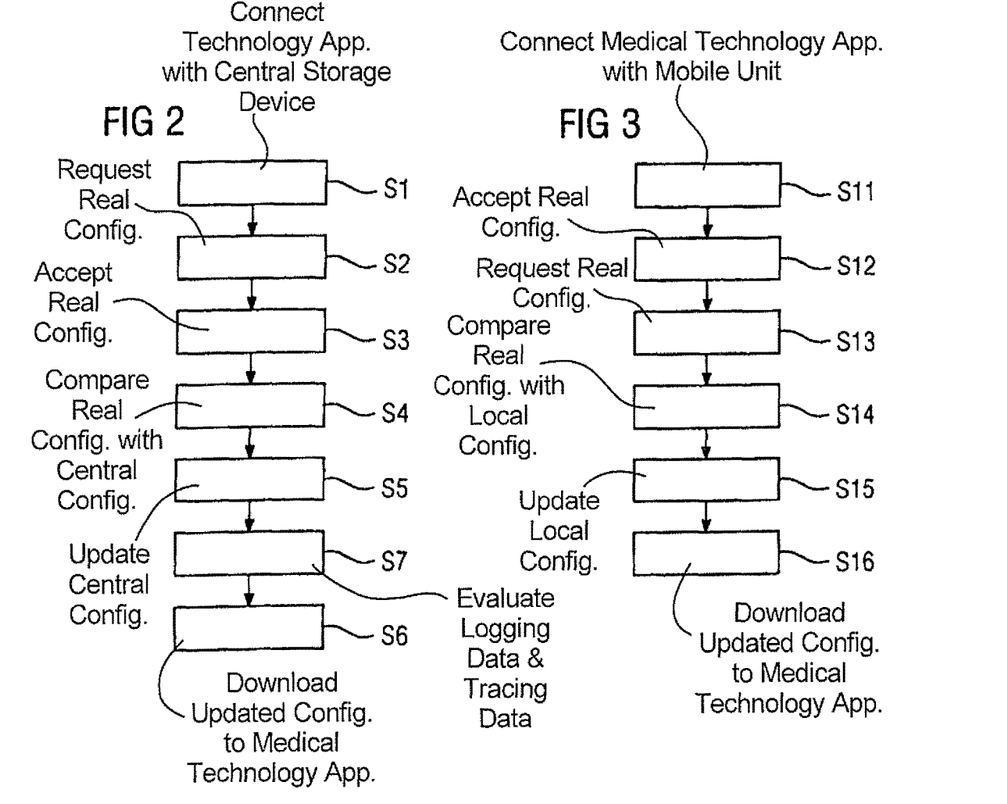
FIGS. 2 to 6 show flowcharts of embodiments of the inventive method.

According to FIG. 2 a data connection of the medical technology apparatus 1 is initially established to the central storage device 2 in a step S1. This connection is established via the computer network 7. Actions taken within the framework of step Si include a mutual authentication of the medical technology apparatus 1 and the central storage device 2. Such authentications are generally known to and trusted by those skilled in the art. Therefore they do not have to be explained in further detail. The communication can in particular take place via a secure connection, for example a virtual private Network (VPN) or another secure protocol.

In a step S2 the central storage device 2 requests from the medical technology apparatus 1 (or from its calculation unit 5) the real configuration K of the medical technology apparatus 1. Then the real configuration K is transferred. The central storage device 2 accepts the real configuration K in a step S3.

In a step S4 the central storage device 2 compares the transferred real configuration K with the central configuration K'. Then, depending on the comparison, the central configuration K' is updated in a step S5. In particular, within the framework of step S5, parts of the central configuration K' are overwritten by the corresponding parts of the real configuration K. As an alternative or in addition, in a step S6, the real configuration K is updated depending on the comparison. In particular, within the framework of step S6, parts of the real configuration K are overwritten by the corresponding parts of the central configuration K'. Independently of the precise method of operation, the steps S5 and S6 are at least as a rule embodied such that, after the updating of the real configuration K and of the central configuration K', the two configurations K, K' match.

It is possible to exchange complete configurations K, K'. As an alternative it is possible to establish in advance the parts of the real configuration K which have to be transferred from the medical technology apparatus 1 to the central storage device 2 or conversely the parts of the central configuration K' which have to be transferred from the central storage device 2 to the medical technology apparatus 1. In this case it is possible to only transfer these parts of the configurations K, K'.

The precise method of operation of steps S4 to S6 will be explained in greater detail below.

Within the framework of step S4 the central storage device 2 checks whether the type identifications of the physical units 4 of the two configurations K, K' match. If this is not the case, either there is an error in the assignment of the configurations K, K' to one another or the physical configuration of the real medical technology apparatus 1 has been changed. If the type identifications match, no further measures are necessary. Otherwise the central storage device 2 generates a message M. The message M is transferred by the central storage device 2 to a computer 11 of the manufacturers of the medical technology apparatus 1 connected to the computer network 7 for example. There, as a result of the message M, a check on the circumstances can be set in train.

Within the framework of step S4 the central storage device 2 also checks whether—provided they are a component of the configurations K, K'—the individual identifications of the physical units 4 match. If the individual identifications match, no further measures are necessary. Otherwise a physical unit 4 has been replaced on the medical technology apparatus 1 side. In this case, in step S5 the associated individual identification of the corresponding physical unit 4 is overwritten in the central configuration K' by the corresponding individual identification of the real configuration K. If the individual identification in the real configuration K is assigned to a point in time at which the corresponding physical unit 4 was installed in the real medical technology apparatus 1, in step S5 the corresponding point in time is also accepted from the real configuration K into the central configuration K'.

Within the framework of step S4 the central storage device 2 also checks the type identifications of the installed software including the software version and also—where this is a component of the configurations K, K'—the update run. If this information matches, no further measures are required. Otherwise additional software and/or a more recent software version for existing software are available on the central storage device 2 side. In this case, within the framework of step S6, the corresponding updates are downloaded from the central storage device 2 into the calculation unit 5 of the medical technology apparatus 1. Together with the download of the updates, within the framework of step S6 on the medical technology apparatus 1 side, an updating of the real configuration K takes place. As a result (inter alia) the type identifications of the installed software, including the software version and if necessary the update run of the real configuration K, are updated by this. After step S6 has been carried out, a match as regards these parts of the configurations K, K' thus exists.

Within the framework of step S4 the central storage device 2 also checks the settings of the medical technology apparatus 1. If the settings match, no further measures are required. Otherwise they must be distinguished from one another. It is possible that specific settings have been made on the medical technology apparatus 1 side, in order to optimize its operation for example. In this case, in step S5 a corresponding adaptation of the central configuration K' is carried out. As an alternative it is possible that new, optimized settings for the medical technology apparatus 1 have been established by the manufacturer of the medical technology apparatus 1 and have been stored in the central configuration K'. In this case the real configuration K is to be adapted. For this, within the framework of step S6, a download of the new, optimized settings to the medical technology apparatus 1 is necessary. The measure that is to be taken in an individual case, depending on the individual setting or associated group of settings, is to be decided individually. It is possible that steps S4, S5 and S6 relating to the settings are carried out interactively with the assistance of the user 6 of the medical technology apparatus 1 and/or of a person skilled in the art 12 of the medical technology apparatus 1 on the central storage device 2 side. It is also possible for example that it is noted on the central storage device 2 side, which setting or group of settings—those of the real configuration K or those of the central configuration K'—have priority in the individual case. In this case the steps S4, S5 and S6 can be carried out automatically in relation to the settings.

Within the framework of step S4 the central storage device 2 also checks the releases of the software of the medical technology apparatus 1. If the releases match, no further measures are required. Otherwise they must be distinguished from one another. It is possible that specific releases have been undertaken on the medical technology apparatus 1 side. In this case, in step S5 a corresponding adaptation of the central configuration K' is performed. As an alternative it is possible that new releases for the software of the medical technology apparatus 1 have been established and stored in the central configuration K' by the manufacturer of the medical technology apparatus 1. In this case—which under some circumstances can be connected with the download of new software—the real configuration K will be adapted. For this, within the framework of step S6, a download of the new releases to the medical technology apparatus 1 is required. Which measure will be taken in the individual case can be decided individually as a function of the individual release or associated group of 3 releases. It is possible for steps S4, S5 and S6 relating to the releases to be carried out interactively with the involvement of the user 6 of the medical technology apparatus 1 and/or of the person skilled in the art 12 of the medical technology apparatus 1 on the central storage device 2 side. It is also possible for example for it to be noted on the central storage device 2 side which release or group of releases—those of the real configuration K or those of the central configuration K'—has priority in the individual case. In this case the steps S4, S5 and S6 relating to the releases can be carried out automatically.

Within the framework of step S4 the central storage device 2 also checks whether the logging data and the tracing data of the two configurations K, K' match. As a rule this will not be the case, because the medical technology apparatus 1 has been used since the last connection to the central storage device 2. If the logging data and the tracing data match, no further measures are required. Otherwise, in step S5, there is a corresponding adaptation of the central configuration K'.

Furthermore, within the framework of a step S7 building on step S5, there can be an evaluation of the logging data and the tracing data. For example, on the basis of the tracing data—where necessary in connection with points in time at which physical units 4 were built into the real medical technology apparatus 1—maintenance information is established and is transferred to the medical technology apparatus 1 within the framework of step S6. The transfer can be made for example in the form of an e-mail, which is written into the e-mail memory of the calculation unit 5 of the medical technology apparatus 1. The maintenance information can be, for example, a reference to a replacement of physical units 4 to be undertaken or to maintenance in the narrower sense. In a similar way, if it is a component of the configuration K, there can also be an evaluation of the user data and analysis for example to establish optimized settings or to check whether maintenance or replacement of physical units 4 is required.

The method of operation of FIG. 2 is carried out when a direct link exists from the medical technology apparatus 1 to the computer network 7. Within the framework of the present invention however no direct link exists from the medical technology apparatus 1 to the computer network 7. This is indicated in FIG. 1 by the linkage of the medical technology apparatus 1 to the computer network 7 only being shown by dashed lines. The method of operation explained above in connection with FIG. 2 is therefore not able to be executed. For this reason the local configuration K' is held on the mobile unit 3. The mobile unit 3 can be connected—at different points in time—on one side to the medical technology apparatus 1 and on the other side to the central storage device 2. Thus the mobile unit 3, by the local configuration K" held in the mobile unit 3, represents the connecting link between the medical technology apparatus 1 and the central storage device 2, so that an updating of the real configuration K and of the central configuration K' is possible, although no direct link exists from the medical technology apparatus 1 to the computer network 7. In order to illustrate this, in conjunction with FIGS. 3 and 4, the communication between the real medical technology apparatus 1 and the mobile unit 3 on the one side and the communication between the central storage device 2 and the mobile unit 3 on the other side will be explained below.

In accordance with FIG. 3, initially in a step S11, a data connection is established from the medical technology apparatus 1 to the mobile unit 3. The step S11 corresponds in Willis of its approach to the step S1 of FIG. 2. The difference that exists, however, is that the connection is not established between the medical technology apparatus 1 and the central storage device 2, but between the medical technology apparatus 1 and the mobile unit 3. One of the actions undertaken in step S11 is a mutual authentication of the medical technology apparatus 1 and the mobile unit 3.

Figure 4:
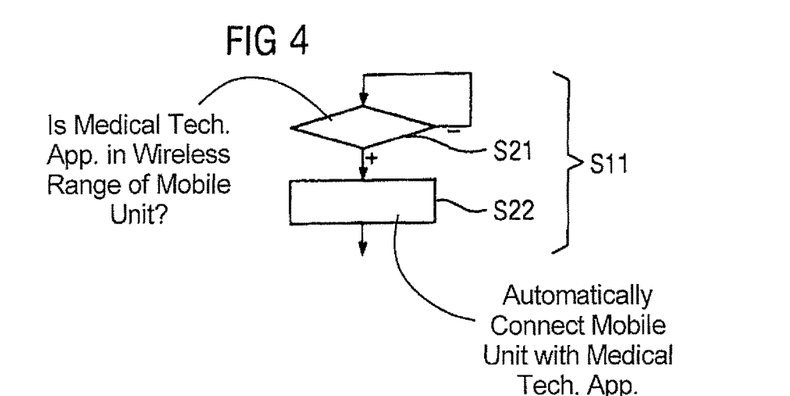

The data connection is preferably a peer-to-peer connection. The connection can be a wired or wireless connection. Preferably, as indicated in FIG. 1 by a lightning bolt symbol, it is a wireless connection, for example a connection in accordance with the Bluetooth standard. In the case of a wireless connection in particular the step S11 can be embodied as depicted in FIG. 4 so that the mobile unit 3 repeatedly checks, in a step S21, whether the medical technology apparatus 1, in relation to the wireless data connection to the medical technology apparatus 1, is located within range of the medical technology apparatus 1. As soon as this is the case, thus as soon the mobile unit 3 is brought within range of the medical technology apparatus 1, the mobile unit 3 in this case goes to a step S22. In step S22 the mobile unit 3 establishes the connection to the medical technology apparatus 1 autonomously.

In a step S12 the mobile unit 3 requests from the medical technology apparatus 1 (or from its calculation unit 5) the real configuration K of the medical technology apparatus 1. The transfer of the real configuration K then takes place. The mobile unit 3 accepts the real configuration K in a step S13. The steps S12 and S13 correspond to the steps S2 and S3 of FIG. 2. The difference that exists however is that the communication partner of the medical technology apparatus 1 is not the central storage device 2 but the mobile unit 3.

In a step S14 the mobile unit 3 compares the transferred real configuration K with the local configuration K". Then, depending on the comparison, in a step S15 an updating of the local configuration K" takes place. As an alternative or in addition, in a step S16, depending on the comparison, an updating of real configuration K takes place. The steps S14 to S16 correspond to the steps S4 to S6 of FIG. 2. The difference that exists, however, is that the communication partner of the medical technology apparatus 1 is not the central storage device 2 but the mobile unit 3.

The communication between the medical technology apparatus 1 and the mobile unit 3 thus takes place from the standpoint of the medical technology apparatus 1 ag if the central storage device 2 were connected to the medical technology apparatus 1. The logic unit 9 thus behaves like the central storage device 2 in relation to the communication with the medical technology apparatus 1. The medical technology apparatus 1 does not "notice" at all that it is not communicating with the central storage device 2 but with the mobile unit 3. Instead it "thinks" that it is communicating with the central storage device 2. The corresponding functionality of the mobile unit 3 is achieved by corresponding programming of the logic unit 9.

Step S7 of FIG. 2 does not have any counterpart in the communication between the medical technology apparatus 1 and the mobile unit 3. However in the narrower sense this is irrelevant for the communication, since the step S7 of FIG. 2 is an internal step carried out by the central storage device 2, which as such does not bring about any communication.

Figure 5:
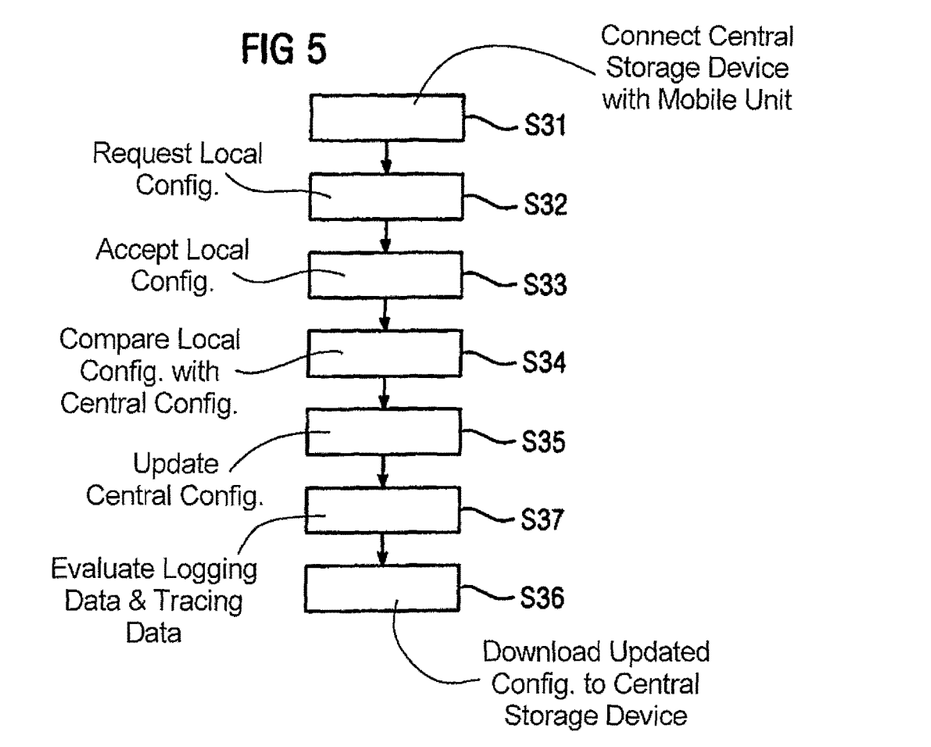

At another point in time in accordance with FIG. 5, in a step S31 a data connection of the mobile unit 3 to the central storage device 2 will be established. The step S31 corresponds in teiiiis of its approach to step S1 of FIG. 2. The difference that exists however is that the connection is not established between the medical technology apparatus 1 and the central storage device 2, but between the mobile unit 3 and the central storage device 2. A mutual authentication of the mobile unit 3 and the central storage device 2 takes place inter alia in step S31. The data connection is preferably made via a link to the computer network 7.

Figure 6:
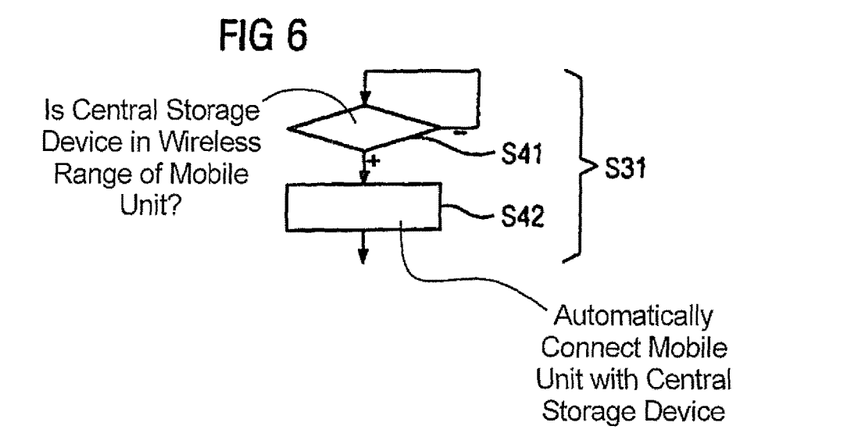

The connection can be made as a wired or wireless connection. A wireless connection is preferred, as is indicated in FIG. 1 by a lightning bolt, for example a connection via an LTE network. In the case of a wireless connection in particular the step S31 as depicted in the diagram in FIG. 6 can be designed such that, in a step S41, the mobile unit 3 checks repeatedly whether the central storage device 2, relative to the wireless data connection to the central storage device 2, is located within range of the central storage device 2. As soon as this is the case, thus as soon as the mobile unit 3 is brought within range of the central storage device 2, the mobile unit 3 moves in this case to a step S42. In step S42 the mobile unit 3 establishes the connection to the central storage device 2 autonomously.

In a step S32 the central storage device 2 requests the local configuration K" of the medical technology apparatus 1 from the mobile unit 3. The local configuration K" is then transferred. The central storage device 2 accepts the local configuration K" in a step S33. The steps S32 and S33 correspond to the steps S2 and S3 of FIG. 2. The difference that exists, however, is that the communication partner of the central storage device 2 is not the medical technology apparatus 1 but the mobile unit 3.

In a step S34 the central storage device 2 compares the transferred local configuration K" with the central configuration K'. Depending on the comparison, the central configuration K' is then updated in a step S35. As an alternative or in addition, in a step S36, the local configuration K" is updated depending on the comparison. The steps S34 to S36 correspond to the steps S4 to S6 of FIG. 2. The difference that exists, however, is that the communication partner of the central storage device 2 is not the medical technology apparatus 1 but the mobile unit 3.

The communication between the central storage device 2 and the mobile unit 3 thus takes place, from the standpoint of the central storage device 2, as if the medical technology apparatus 1 were connected to the central storage device 2. The logic unit 9 thus behaves, in relation to the communication with the central storage device 2, like the real medical technology apparatus 1. The central storage device 2 does not "notice" at all that it is not communicating with the medical technology apparatus 1 but with the mobile unit 3. Instead it "thinks" that it is communicating with the medical technology apparatus 1. The corresponding functionality of the mobile unit 3 is achieved by corresponding programming of the logic unit 9.

The step S7 of FIG. 2 likewise has a counterpart in FIG. 5. The corresponding step is labeled S37 in this figure.

Through this method of operation, that sometimes the method of operation according to FIG. 3 is thus carried out and sometimes the method of operation according to FIG. 5 is carried out, it is thus possible to undertake a mutual updating of the real configuration K and/or of the central configuration K", although at no point in time does a direct connection between the medical technology apparatus 1 and the central storage device 2 exist.

It is not absolutely necessary for each connection of the mobile unit 3 to the medical technology apparatus 1 to be followed by a connection of the mobile unit 3 to the central storage device 2 and conversely for each connection of the mobile unit 3 to the central storage device 2 to be followed by a connection of the mobile unit 3 to the medical technology apparatus 1. Instead it is possible to connect the mobile unit 3 a number of times in succession to the medical technology apparatus 1, to undertake the mutual updating of real configuration K and local configuration K" in each case and only thereafter to connect the mobile unit 3 again to the central storage device 2 and then to carry out the mutual updating of local configuration K" and central configuration K'. It is conversely possible to connect the mobile unit 3 a number of times in succession to the central storage device 2, to undertake the mutual updating of local configuration K" and central configuration K' in each case and only thereafter to connect the mobile unit 3 again to the medical technology apparatus 1 and then to undertake the mutual updating of real configuration K and local configuration K". The decisive factor is that the mobile unit 3 can perform the agent function between the medical technology apparatus 1 and the central storage device 2. In the individual case it can even be possible to connect the mobile unit 3 simultaneously both to the medical technology apparatus 1 and also to the central storage device 2. In this case a dual communication takes place simultaneously from the standpoint of the mobile unit 3, namely with the medical technology apparatus 1 on one side and with the central storage device 2 on the other side.

The present invention has further been explained above in connection with a mobile unit 3, which comprises a logic unit 9 comprises and is thus capable of assuming an active role in the updating of the configurations K, K', K". As an alternative it is possible for the mobile unit 3 not to include any such logic unit 9 (and then also no user interface 10). In this case, provided the updating of the real configuration K and of the local configuration K" is involved, the corresponding functions must be taken over by the medical technology apparatus 1 or by its calculation unit 5 and are also performed in the medical technology apparatus 1 or its calculation unit 5. Where the updating of the local configuration K" and of the central configuration K' are involved, the corresponding measures can continue to be handled by the central storage device 2. The mobile unit 3 can in this case alternately be linked directly to the computer network 7 or via an intermediate device, to which the mobile unit 3 is connected. The intermediate device can be a laptop or a PC for example.

In summary the present invention thus involves the following subject matter:

A mobile unit 3 comprises a memory 8. The mobile unit 3 is connected for data transfer for a time to the medical technology apparatus 1 and for a time to the central storage device 2. When the mobile unit 3 is connected to the medical technology apparatus 1, a real configuration K of the medical technology apparatus 1 is compared with a local virtual image K" of the configuration K of the medical technology apparatus 1 (=local configuration K") held in the memory 8 of the mobile unit 3. Depending on this comparison the local configuration K" and/or the real configuration K are updated. When the mobile unit 3 is connected to the central storage device 2, the local configuration K" is compared with a central virtual image K' of the configuration K of the medical technology apparatus 1 (=central configuration K'). Depending on this comparison the central configuration K' and/or the local configuration K" are updated. Using the intermediary of the local configuration K", this enables the real configuration K and the central configuration K' to be mutually updated.

The present invention has many advantages. The inventive method of operation makes updating of the real and the central configuration K, K' possible, even if no direct connection exists between the medical technology apparatus 1 and the central storage device 2. Furthermore the mutual updating is able to be automated to a high degree. Possible errors are greatly reduced. The mutual updating is also significantly speeded up. The updating can also be carried out by people who are not computer specialists. This is particularly of advantage for the mutual updating between the medical technology apparatus 1 and the mobile unit 3.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for updating at least one of a real configuration of a medical technology apparatus or a central virtual image of the configuration of a medical technology apparatus stored in a central storage data base, said method comprising:
   (a) temporarily connecting a mobile communication unit, comprising a memory in which a local virtual image of a configuration of a medical technology apparatus is stored, to said medical technology apparatus having a real configuration, and temporarily connecting said mobile communication unit to a central storage data base in which a central virtual image of the configuration of the medical technology apparatus is stored;
   (b) while said mobile communication unit is connected to said medical technology apparatus, transferring the real configuration from the medical technology apparatus to the mobile communication unit and comparing, in said mobile communication unit, the real configuration of the medical technology apparatus to said virtual image of a configuration of the medical technology apparatus in the memory of the mobile communication unit, obtaining a first comparison result and, dependent on said first comparison result, updating at least one of said local virtual image or said real configuration and matching said local virtual image and said real configuration; and
   (c) while said mobile communication unit is temporarily connected to said central storage data base transferring the central virtual images of the configuration of the medical technology apparatus from the central storage data base to the mobile communication unit and, comparing, in said mobile communication unit, the local virtual image in the memory of the mobile communication unit with the central virtual image in said central storage data base, obtaining a second comparison result and, dependent on said second comparison result, updating at least one of said central virtual image or said local virtual image, matching said central virtual image and said local virtual image, and matching said central virtual image and said real configuration.

2. A method as claimed in claim 1 comprising connecting said mobile communication unit for data communication to each of said medical technology apparatus and said central storage data base via a peer-to-peer connection.

3. A method as claimed in claim 1 comprising connecting said mobile communication unit to said central storage data base via a link to a computer network for said data transmission.

4. A method as claimed in claim 1 wherein said mobile communication unit comprises a processor and, when said mobile communication unit is temporarily connected to said medical technology apparatus, using said processor to communicate with said medical technology apparatus as said central storage data base, and when said mobile communication unit is temporarily connected to said central storage device, using said processor to communicate with said central storage data base as said medical technology apparatus.

5. A method as claimed in claim 4 comprising implementing said data connection between said mobile communication unit and said medical technology apparatus wirelessly and, via said mobile communication unit, autonomously establishing said data communication connection with said medical technology apparatus as soon as said mobile communication unit, relative to the wireless data connection to the medical technology apparatus, is brought within range of the medical technology apparatus.

6. A method as claimed in claim 4 comprising implementing said data connection between said mobile communication unit and said central storage data base wirelessly, and, with said mobile communication unit, autonomously establishing said data connection with the medical technology apparatus as soon as the mobile communication unit, relative to the wireless data connection to the central storage data base, is brought within range of the central storage data base.

7. A mobile communication unit for updating at least one of a real configuration of a medical technology apparatus or a central virtual image of the configuration of a medical technology apparatus stored in a central storage data base, said mobile communication unit comprising:
 a memory in which a local virtual image of a configuration of a medical technology apparatus is stored;
 an interface configured to temporarily connect said memory to said medical technology apparatus having a real configuration, and to temporarily connect said memory to a central storage data base in which a central virtual image of the configuration of the medical technology apparatus is stored;
 a processor configured, while said mobile communication unit is connected to said medical technology apparatus, to transfer the real configuration from the medical technology apparatus to the mobile communication unit and to compare the real configuration of the medical technology apparatus to said virtual image of a configuration of the medical technology apparatus in the memory of the mobile communication unit, obtaining a first comparison result and, dependent on said first comparison result, to implement a first update of at least one of said local virtual image or said real configuration and matching said local virtual image and said real configuration; and
 said processor being configured, while said mobile communication unit is temporarily connected to said central storage data base, to transfer the central virtual images of the configuration of the medical technology apparatus from the central storage data base to the mobile communication unit and to compare the local virtual image in the memory of the mobile communication unit with the central virtual image in said central storage data base, obtaining a second comparison result and, dependent on said second comparison result, to implement a second update of at least one of said central virtual image or said local virtual image, matching said central virtual image and said local virtual, image and matching said central virtual image and said real configuration.

8. A mobile communication unit as claimed in claim 7 wherein said interface is configured to connect said mobile communication unit for data communication to each of said medical technology apparatus and said central storage data base via a peer-to-peer connection.

9. A mobile communication unit as claimed in claim 7 wherein said interface is configured to connect said mobile communication unit to said central storage data base via a link to a computer network for said data transmission.

10. A mobile communication unit as claimed in claim 7 wherein said interface is configured to implement said data connection between said memory and said medical technology apparatus wirelessly and to autonomously establish said data communication connection with said medical technology apparatus as soon as said mobile communication unit, relative to the wireless data connection to the medical technology apparatus, is brought within range of the medical technology apparatus.

11. A mobile communication unit as claimed in claim 7 wherein said interface is configured to implement said data connection between said memory and said central storage data base wirelessly autonomously establish said data connection with the medical technology apparatus as soon as the mobile communication unit, relative to the wireless data connection to the central storage data base, is brought within range of the central storage data base.

12. A mobile communication unit as claimed in claim 7 configured as at least one of a smartphone, a tablet PC, a notebook, a laptop, and a PC.

* * * * *